(12) United States Patent
Hann

(10) Patent No.: US 11,816,264 B2
(45) Date of Patent: Nov. 14, 2023

(54) VITAL DATA ACQUISITION AND THREE-DIMENSIONAL DISPLAY SYSTEM AND METHOD

(71) Applicant: Smart Beat Profits Limited, Shau Kei Wan (HK)

(72) Inventor: Lian Yih Hann, Sheung Wan (HK)

(73) Assignee: SMART BEAT PROFITS LIMITED, Hong Kong (CN)

( * ) Notice: Subject to any disclaimer, the term of this patent is extended or adjusted under 35 U.S.C. 154(b) by 0 days.

(21) Appl. No.: 16/620,404

(22) PCT Filed: Jun. 7, 2018

(86) PCT No.: PCT/JP2018/021936
§ 371 (c)(1),
(2) Date: Dec. 6, 2019

(87) PCT Pub. No.: WO2018/225838
PCT Pub. Date: Dec. 13, 2018

(65) Prior Publication Data
US 2020/0133394 A1    Apr. 30, 2020

(30) Foreign Application Priority Data
Jun. 7, 2017 (JP) .................. 2017-112845

(51) Int. Cl.
*G06F 3/01* (2006.01)
*G06T 13/40* (2011.01)

(52) U.S. Cl.
CPC .............. *G06F 3/015* (2013.01); *G06T 13/40* (2013.01); *G06F 2203/011* (2013.01)

(58) Field of Classification Search
None
See application file for complete search history.

(56) References Cited

U.S. PATENT DOCUMENTS 6,354,679 B1    3/2002 Maguire et al. .............. 305/201
9,930,102 B1 *  3/2018 Paulus .................. G06Q 10/10
(Continued)

FOREIGN PATENT DOCUMENTS

CN           106126895        11/2016   ............. G06F 19/00
EP          3117766 A1 *      1/2017   ......... A61B 5/02405
(Continued)

*Primary Examiner* — Jeffrey J Chow
(74) *Attorney, Agent, or Firm* — Slayden Grubert Beard PLLC

(57) ABSTRACT

Provided is an information processing system capable of configuring an avatar that more realistically reflects a state of a user. The information processing system includes: vital data acquiring means for acquiring vital data including a heart rate of a user; a terminal apparatus that transmits, in real-time via a communication network, the vital data acquired by the vital data acquiring means; and an information processing server that processes the vital data transmitted from the terminal apparatus, wherein the information processing server includes: a storage unit that stores the vital data; a user state estimating unit that estimates a state of the user based on at least the heart rate and a heart rate variability calculated, based on the heart rate; an avatar data creating unit that creates display data for displaying an avatar reflecting at least an estimation result by the user state estimating unit; and a communication interface that, when a transmission request for the display data is received via the communication network, transmits the display data to a source of the transmission request.

11 Claims, 12 Drawing Sheets

(56) References Cited

U.S. PATENT DOCUMENTS

| | | | |
|---|---|---|---|
| 2005/0042589 A1* | 2/2005 | Hatlestad | A61B 5/4818 434/262 |
| 2007/0050715 A1* | 3/2007 | Behar | A61B 5/7475 715/706 |
| 2009/0040231 A1 | 2/2009 | Sano | 345/474 |
| 2009/0105560 A1* | 4/2009 | Solomon | G16H 40/67 600/301 |
| 2011/0124977 A1* | 5/2011 | Winarski | G06F 3/015 600/301 |
| 2011/0184248 A1 | 7/2011 | Furuat | A61B 5/00 |
| 2012/0083675 A1 | 4/2012 | Kaliouby | A61B 5/0205 |
| 2012/0083714 A1 | 4/2012 | Yuen | 600/587 |
| 2013/0115582 A1* | 5/2013 | el Kaliouby | G06F 19/3481 434/237 |
| 2015/0038806 A1 | 2/2015 | Kaleal | 600/301 |
| 2015/0112797 A1* | 4/2015 | Short | C12Q 1/6883 707/738 |
| 2015/0199494 A1* | 7/2015 | Koduri | G06F 19/3481 700/91 |
| 2015/0206000 A1* | 7/2015 | el Kaliouby | G06F 3/005 382/118 |
| 2016/0082979 A1* | 3/2016 | Seder | G08C 17/02 340/933 |
| 2016/0277911 A1 | 9/2016 | Kang | H04W 4/22 |
| 2016/0379511 A1* | 12/2016 | Dawson | G06F 3/0482 434/362 |
| 2017/0068790 A1* | 3/2017 | Fuerst | G16H 40/67 |
| 2017/0337350 A1* | 11/2017 | Kim | A61B 5/0015 |
| 2017/0367651 A1* | 12/2017 | Tzvieli | A61B 5/0075 |
| 2018/0132789 A1* | 5/2018 | Chen | A61B 5/6826 |
| 2018/0301054 A1* | 10/2018 | Banerji | A61B 5/165 |
| 2021/0142894 A1* | 5/2021 | Raisanen | A61B 5/681 |
| 2021/0153756 A1* | 5/2021 | Hubner | A61B 5/6898 |
| 2021/0204867 A1* | 7/2021 | Toth | A61B 5/1102 |
| 2022/0095931 A1* | 3/2022 | Stahmann | A61B 5/7275 |

FOREIGN PATENT DOCUMENTS

| | | | |
|---|---|---|---|
| JP | 2000285377 A | 10/2000 | G08B 25/10 |
| JP | 2001347972 A | 12/2001 | B62D 55/088 |
| JP | 2004062364 A | 2/2004 | G06Q 50/00 |
| JP | 2004-246535 A | 9/2004 | G06F 17/30 |
| JP | 2005057343 A | 3/2005 | G06Q 40/08 |
| JP | 2006 120137 | 5/2006 | G08G 1/09 |
| JP | 2009-502335 A | 1/2009 | A61B 5/00 |
| JP | 2011-154565 A | 8/2011 | G06F 3/038 |
| JP | 2011204116 A | 10/2011 | G06Q 40/00 |
| JP | 2013-258555 A | 12/2013 | H04N 5/64 |
| JP | 2014-504460 A | 2/2014 | H04N 21/258 |
| JP | 2016-126500 A | 7/2016 | G06F 3/01 |
| WO | 2014/145228 | 9/2014 | G06Q 50/22 |

* cited by examiner

| USER ID | USER NAME | PASSCODE | ACCESS RESTRICTION |
|---|---|---|---|
| xxxxxxx | xxx xxx | 123xx45xx | NONE |
| yyyyyyy | yyyy yy | yy789yy | LEVEL 2 |
| zzzzzzz | zzzz zzz | 123456xyz | LEVEL 3 |
| ⋮ | ⋮ | ⋮ | ⋮ |

|  |  | DATA A | | | | | |
|---|---|---|---|---|---|---|---|
|  |  | 1 | 2 | 3 | 4 | 5 | 6 | ... |
| DATA B | 1 | | | | | | |
| | 2 | | | | | | |
| | 3 | | | | | | |
| | 4 | | | | | X1 | |
| | 5 | | | | | | |
| | 6 | | | | | | |
| | ⋮ | | | | | | |

|   | A | B | C | D | E | F | ... | TOTAL |
|---|---|---|---|---|---|---|-----|-------|
| A |   | 3 | 8 | 5 |   |   |     | 16    |
| B | 2 |   |   |   | 6 | 4 |     | 12    |
| ⋮ |   |   |   |   |   |   |     |       |

VITAL DATA ACQUISITION AND THREE-DIMENSIONAL DISPLAY SYSTEM AND METHOD

TECHNICAL FIELD

The present invention relates to an information processing system which collects and visualizes information relating to a living body.

BACKGROUND ART

Recently, techniques for collecting information relating to a user that is a living body using various sensors and visualizing the information by reflecting the information in an avatar and displaying the avatar are known. In this case, an avatar refers to "a character that appears on computer networks in place of a user" ("The Yearbook of the Contemporary Society 2017"; Jiyukokuminsha; page 1231).

For example, Patent Document 1 discloses a technique for measuring emotion data with respect to a web-enabled application. Specifically, based on electrodermal activity (EDA), a reading of an accelerometer, physiological data such as skin temperature, or a facial expression or a head gesture observed by a web camera, a mental state of a user when interacting with a website or a rendering of a video or the like is estimated and information on the mental state is associated with the rendering. In addition, according to Patent Document 1, the mental state information is displayed using a visual representation such as an avatar.

Patent Document 2 discloses a technique for detecting potential at a plurality of locations on the head of a user or detecting an acceleration or an angular velocity of the head of the user, estimating a movement of the head and/or a facial expression based on detection results thereof, and imparting the estimated facial expression to an avatar together with the movement of the head and displaying the avatar on a display.

CITATION LIST

Patent Documents

Patent Document 1: Japanese Translation of PCT Application No. 2014-504460
Patent Document 2: Patent Publication JP-A-2016-126500

SUMMARY

Technical Problem

In both Patent Documents 1 and 2, an avatar is used as means of communication by displaying a mental state or a facial expression of a user on the avatar. However, with the spread of remote communication and the emergence of a wide variety of applications in recent years, it is expected that methods of utilizing avatars will also become more diversified and sophisticated. To this end, it is desired that avatars be configured which not only reflect a simple mental state or a simple facial expression of a user such as happy or sad but also more realistically reflect a state of the user.

The present invention has been made in consideration of such circumstances, and an object thereof is to provide an information processing system capable of configuring an avatar which more realistically reflects a state of a user.

Solution to Problem

In order to solve the problem described above, an information processing system according to an aspect of the present invention includes: vital data acquiring means that acquires vital data including at least a heart rate of a user; a terminal apparatus that transmits, in real-time via a communication network, the vital data acquired by the vital data acquiring means; and an information processing server that processes the vital data transmitted from the terminal apparatus, wherein the information processing server includes: a storage unit that stores the vital data; a user state estimating unit that estimates a state of the user in real-time, based on at least the heart rate and a heart rate variability calculated based on the heart rate; an avatar data creating unit that creates display data for displaying an avatar reflecting at least an estimation result by the user state estimating unit; and a communication interface that, when a transmission request for the display data is received via the communication network, transmits the display data to a source of the transmission request.

In the information processing system described above, the user state estimating unit may estimate a mental state of the user, and the avatar data creating unit may create display data on the avatar reflecting the mental state of the user.

In the information processing system described above, the avatar data creating unit may create display data in which a facial expression or a posture of the avatar is changed in accordance with the mental status of the user.

In the information processing system described above, the avatar data creating unit may create display data in which a color or a display range of an aura of the avatar is changed in accordance with the mental state of the user.

In the information processing system described above, the user state estimating unit may estimate a state of health of the user, and the avatar data creating unit may create display data on the avatar reflecting the state of health of the user.

In the information processing system described above, the avatar data creating unit may create display data in which a color of the avatar is partially changed in accordance with the state of health of the user.

In the information processing system described above, the avatar data creating unit may create display data in which a color or a display range of an aura of the avatar is changed in accordance with the state of health of the user.

In the information processing system described above, the user state estimating unit may estimate a state of activity of the user, and the avatar data creating unit may create display data on the avatar reflecting the state of activity of the user.

In the information processing system described above, the avatar data creating unit may create display data in which a shape of the avatar is changed in accordance with the state of activity of the user.

In the information processing system described above, the display data is three-dimensional data including information relating to an inside of the avatar, and display data for displaying the inside of the avatar may be created and transmitted to the request source in response to a transmission request for the display data from the request source.

In the information processing system described above, the vital data acquiring means may further acquire vital data on a different type from the heart rate, the information processing server may further include a correlation analyzing unit which analyzes a correlation among pieces of vital data on a plurality of types that differ from each other, and the user state estimating unit may further estimate a state of the user, based on an analysis result by the correlation analyzing unit.

Advantageous Effects of Invention

According to the present invention, since vital data which at least includes a heart rate of a user is acquired, a state of the user is estimated in real-time based on the vital data, and display data for an avatar reflecting an estimation result thereof is created, an avatar more realistically reflecting a state of a user can be configured.

BRIEF DESCRIPTION OF DRAWINGS

FIG. 4 is a schematic diagram illustrating information stored in a user management database stored in a storage unit shown in FIG. 3.

FIG. 6 is a schematic diagram illustrating information stored in a correlation information database stored in the storage unit shown in FIG. 3.

DESCRIPTION OF EMBODIMENTS

An embodiment of the present invention will now be described in detail. The embodiment described below is for illustrative purposes only and is not intended to limit the present invention thereto. In addition, various modifications can be made to the present invention without departing from the scope of the invention. It will thus be appreciated that those skilled in the art will be able to adopt embodiments in which the respective elements described below are replaced by equivalents and that such embodiments will also fall within the scope of the present invention.

(1) Configuration of Embodiment

Figure 1:
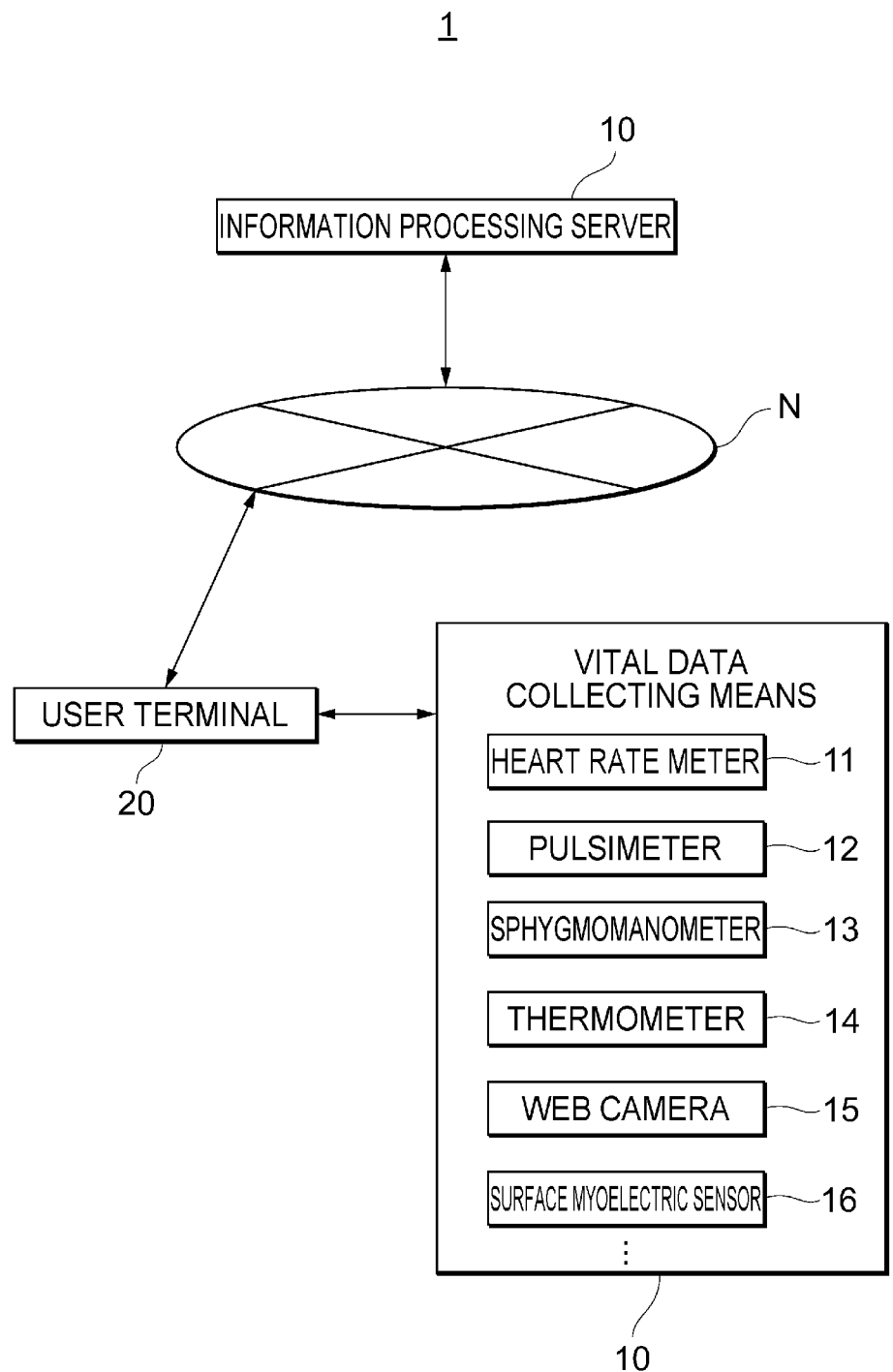
FIG. 1 is a system block diagram schematically showing an example of an information processing system according to an embodiment of the present invention.

FIG. 1 is a system block diagram schematically showing an example of an information processing system according to the embodiment of the present invention. As shown in FIG. 1, an information processing system 1 includes vital data collecting means 10 which collects vital data that is living body information of a user, a user terminal 20, and an information processing server 30. Among these elements, the user terminal 20 and the information processing server 30 are connected via a communication network N (however, this configuration is not restrictive).

The network N is a communication network constituted by the Internet, a LAN, a dedicated line, a telephone line, an intranet, a mobile communication network, Bluetooth (registered trademark), WiFi (Wireless Fidelity), other communication lines, or a combination thereof, and may be either a wired network or a wireless network.

The vital data collecting means 10 includes a plurality of devices which are mounted to the body of the user or installed around the body of the user and which monitor the body of the user to collect vital data. Specifically, in addition to a heart rate meter 11 which measures a heart rate of the user, the vital data collecting means 10 includes a pulsimeter 12, a sphygmomanometer 13, a thermometer 14, a web camera 15 which photographs a movement of the face or the body of the user, and a surface myoelectric sensor 16 which measures a movement of muscles of the user. One or a plurality of each device may be provided. For example, mounting a plurality of the pulsimeters 12 to a plurality of locations on the body of the user can improve measurement accuracy. Other than the above, a microphone for collecting the voice of the user, a pedometer, and the like may be provided as the vital data collecting means 10.

Figure 2:
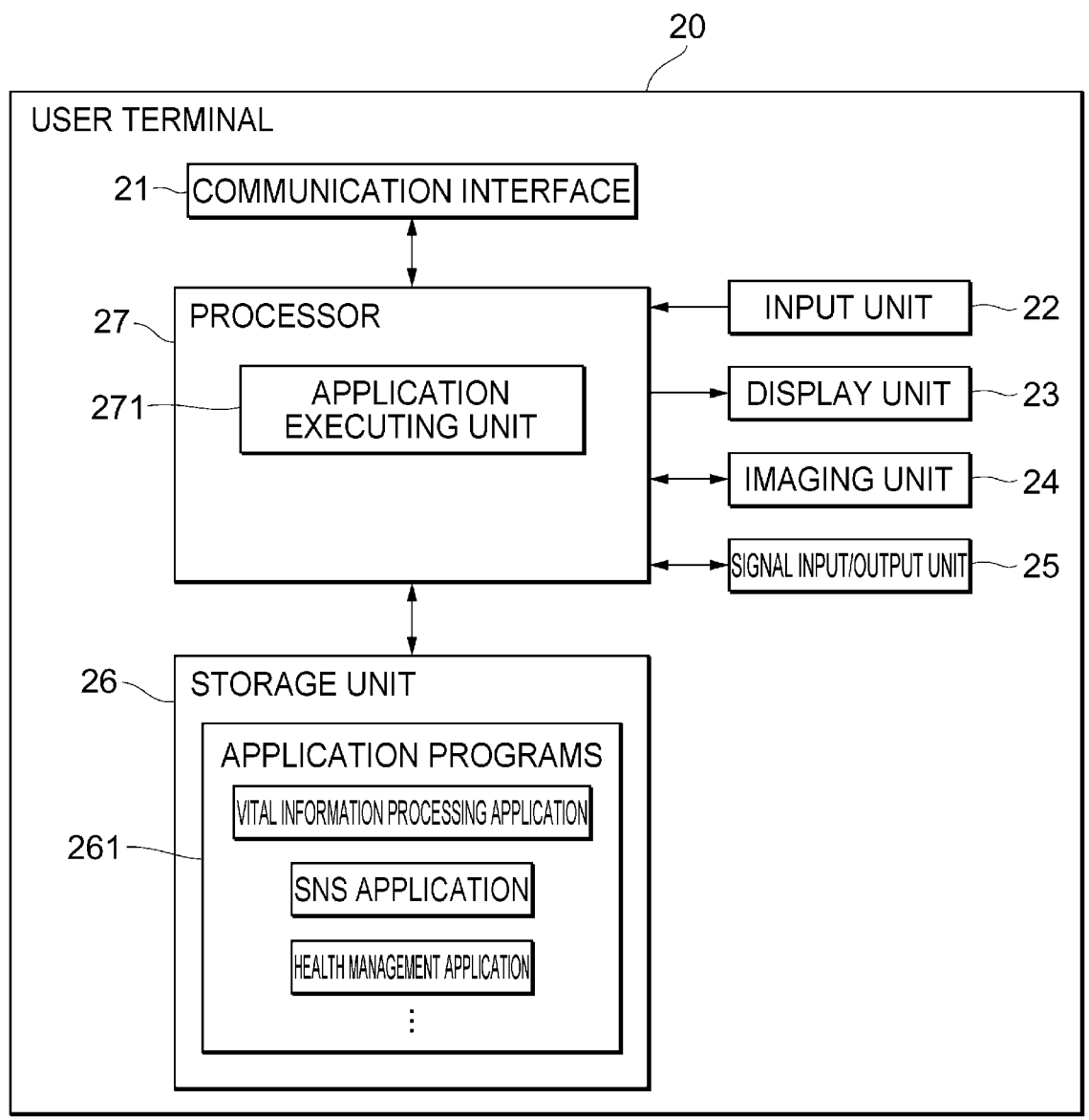
FIG. 2 is a system block diagram schematically showing an example of a configuration of a user terminal shown in FIG. 1.

FIG. 2 is a system block diagram schematically showing an example of a configuration of the user terminal 20 in the information processing system according to the embodiment of the present invention. As the user terminal 20, any terminal apparatus capable of exchanging data with other communication devices via a communication network such as a tablet terminal, a personal computer (PC), a notebook PC, a smartphone, a mobile phone, or a personal digital assistance (PDA) can be used. In the present embodiment, by installing a dedicated application to a tablet terminal and executing the application, the tablet terminal is used as the user terminal 20.

The user terminal 20 is provided with a communication interface 21, an input unit 22, a display unit 23, an imaging unit 24, a signal input/output unit 25, a storage unit 26, and a processor 27.

The communication interface 21 is a hardware module for connecting the user terminal 20 to the communication network N to communicate with other terminals on the communication network N. For example, the communication interface 21 is a modulator-demodulator such as an ISDN modem, an ADSL modem, a cable modem, an optical modem, or a software modem.

The input unit 22 is an input device such as various operation buttons or a touch panel. The display unit 23 is, for example, a liquid crystal display or an organic EL display. The imaging unit 24 is a camera built into the tablet terminal.

The signal input/output unit 25 is an interface for connecting an external device to the user terminal 20 by wired (cable) communication or wireless communication based on a standard such as Bluetooth (registered trademark) to transmit and receive signals to and from the external device. In the present embodiment, the respective devices included in the vital data collecting means 10 are connected to the user terminal 20 via the signal input/output unit 25.

The storage unit 26 is a logical device provided by a storage region of a physical device and stores an operating system program, a driver program, and various types of data to be used in processes of the user terminal 20. In this case, a physical device refers to a computer-readable storage medium such as a semiconductor memory. Examples of driver programs include a communication interface driver program for controlling the communication interface 21, an input device driver program for controlling the input unit 22, a display device driver program for controlling the display unit 23, an imaging device driver program for controlling the imaging unit 24, and various driver programs for controlling external devices connected to the signal input/output unit 25.

In addition to the various programs and various types of data described above, the storage unit 26 stores a dedicated application program 261 which, when executed by the processor 27, executes a prescribed operation in cooperation with the information processing server 30. Examples of the application program 261 include an application program for processing vital data collected by the vital data collecting means 10 (a vital information processing application), an application program for an SNS (a social networking service) (an SNS application), and an application program for managing the health of the user (a health management application).

The processor 27 is constituted by an arithmetic logic operation unit (a CPU or the like) that processes arithmetic operations, logic operations, bit operations, and the like and various registers, and controls the respective units of the user terminal 20 in a concentrated manner by executing the various programs stored in the storage unit 26. Examples of the various registers include a program counter, a data register, an instruction register, and a general-purpose register. In addition, the processor 27 reads the application program 261 and functions as an application executing unit 271 which executes applications for vital information processing, SNS, health management, and the like.

Such a user terminal 20 favorably receives various pieces of vital data output from the vital data collecting means 10 and transmits the vital data to the information processing server 30 constantly and in real-time via the communication network N.

In the present embodiment, the vital data collecting means 10 is connected to the user terminal 20, and vital data is transmitted to the information processing server 30 via the user terminal 20. Alternatively, each vital data collecting means 10 may be provided with a communication function and, at the same time, an identification code (ID) of each vital data collecting means 10 may be registered in the information processing server 30 in advance, in which case vital data may be directly transmitted from each vital data collecting means 10 to the information processing server 30.

In addition, while FIG. 1 illustrates one of each of the vital data collecting means 10 and the user terminal 20, this configuration is not restrictive. In other words, two or more user terminals 20 to which the vital data collecting means 10 is respectively connected can be connected to the communication network N, and the information processing server 30 can be simultaneously accessed from the respective user terminals 20.

Figure 3:
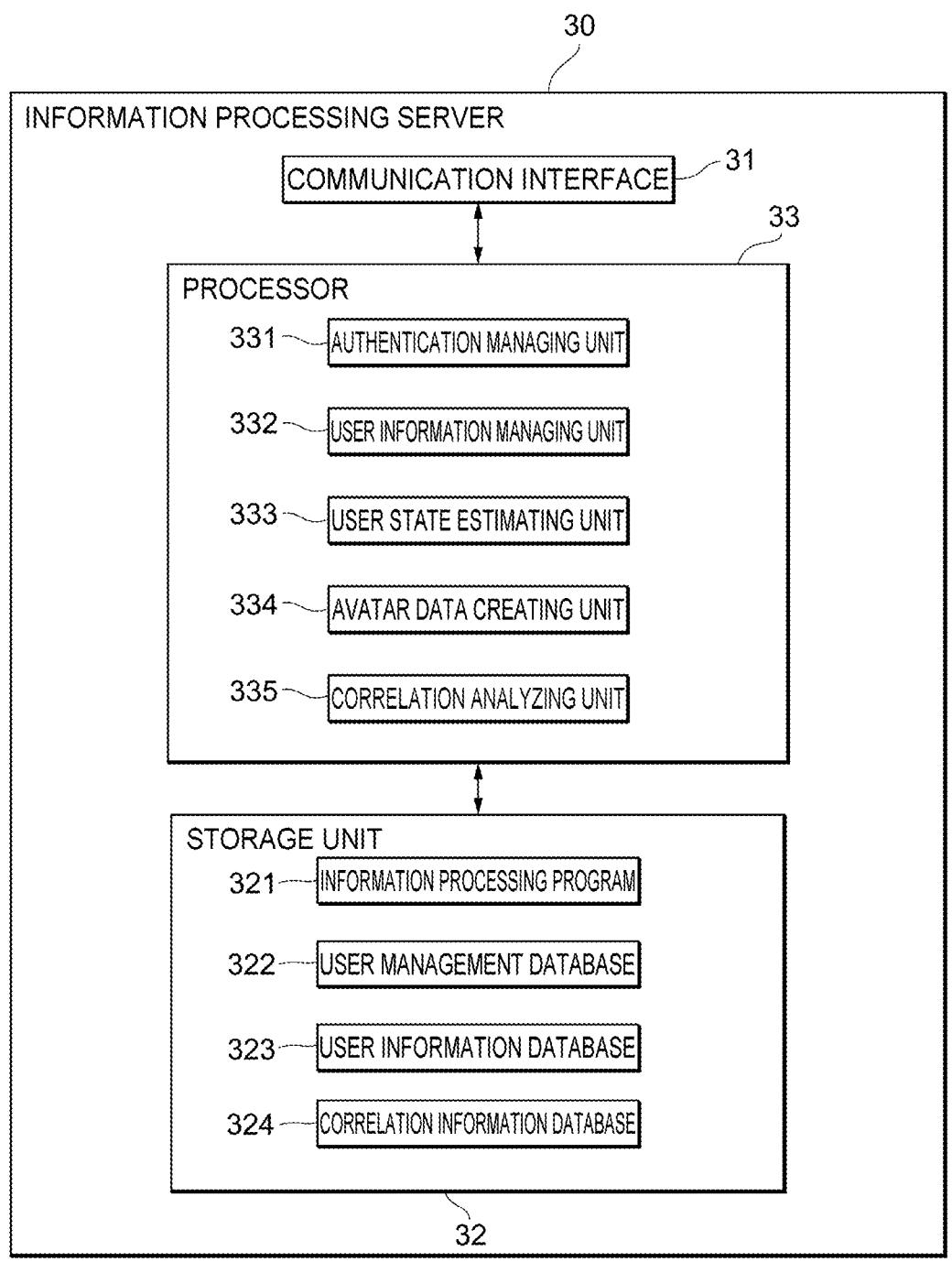
FIG. 3 is a system block diagram schematically showing an example of a configuration of an information processing server shown in FIG. 1.

FIG. 3 is a system block diagram schematically showing an example of a configuration of the information processing server in the information processing system according to the embodiment of the present invention. The information processing server 30 is a server apparatus which accumulates vital data transmitted from the user terminal 20 (or the vital data collecting means 10), which estimates a state of the user in real-time based on the accumulated vital data, and which visualizes the state of the user and provides the user terminal 20 with the visualized state of the user in response to a request from the user terminal 20. For example, the information processing server 30 is constituted by a host computer with high arithmetic processing capacity, and a server function is exhibited as a prescribed server program runs on the host computer. Moreover, the information processing server 30 need not necessarily be constituted by a single computer and may be constituted by a plurality of computers distributed on the communication network N.

The information processing server 30 is provided with a communication interface 31, a storage unit 32, and a processor 33.

The communication interface 31 is a hardware module for connecting to the communication network N to communicate with other terminals on the communication network N. Specifically, for example, the communication interface 31 is a modulator-demodulator such as an ISDN modem, an ADSL modem, a cable modem, an optical modem, or a software modem.

The storage unit 32 is, for example, a logical device provided by a storage region of a physical device constituted by a computer-readable storage medium such as a disk drive or a semiconductor memory (a ROM, a RAM, or the like). The storage unit 32 may be constructed by mapping a plurality of physical devices to one logical device or by mapping one physical device to a plurality of logical devices. The storage unit 32 stores various programs including an operating system program and a driver program as well as various types of data to be used when executing the programs. Specifically, the storage unit 32 stores an information processing program 321 to be executed by the processor 33, a user management database 322, a user information database 323, and a correlation information database 324.

The information processing program 321 is a program to be executed by the processor 33 in order to realize a function of accumulating vital data on a user and visualizing and providing a state of the user (a mental state, a state of health, a state of activity, or the like) based on the accumulated vital data.

FIG. 4 is a schematic diagram illustrating information stored in the user management database 322. The user management database 322 stores account information of a user including a user ID, a user name, and a passcode, and information for managing access restrictions. An access restriction restricts, when a request to browse information relating to the user is submitted by another user, a range of information to be disclosed to the other user. Access restrictions can be set in stages by the user in a range from "full disclosure (no access restriction)" to "only disclosed to user himself/herself" depending on a relationship between the user and the other user.

Figure 5:
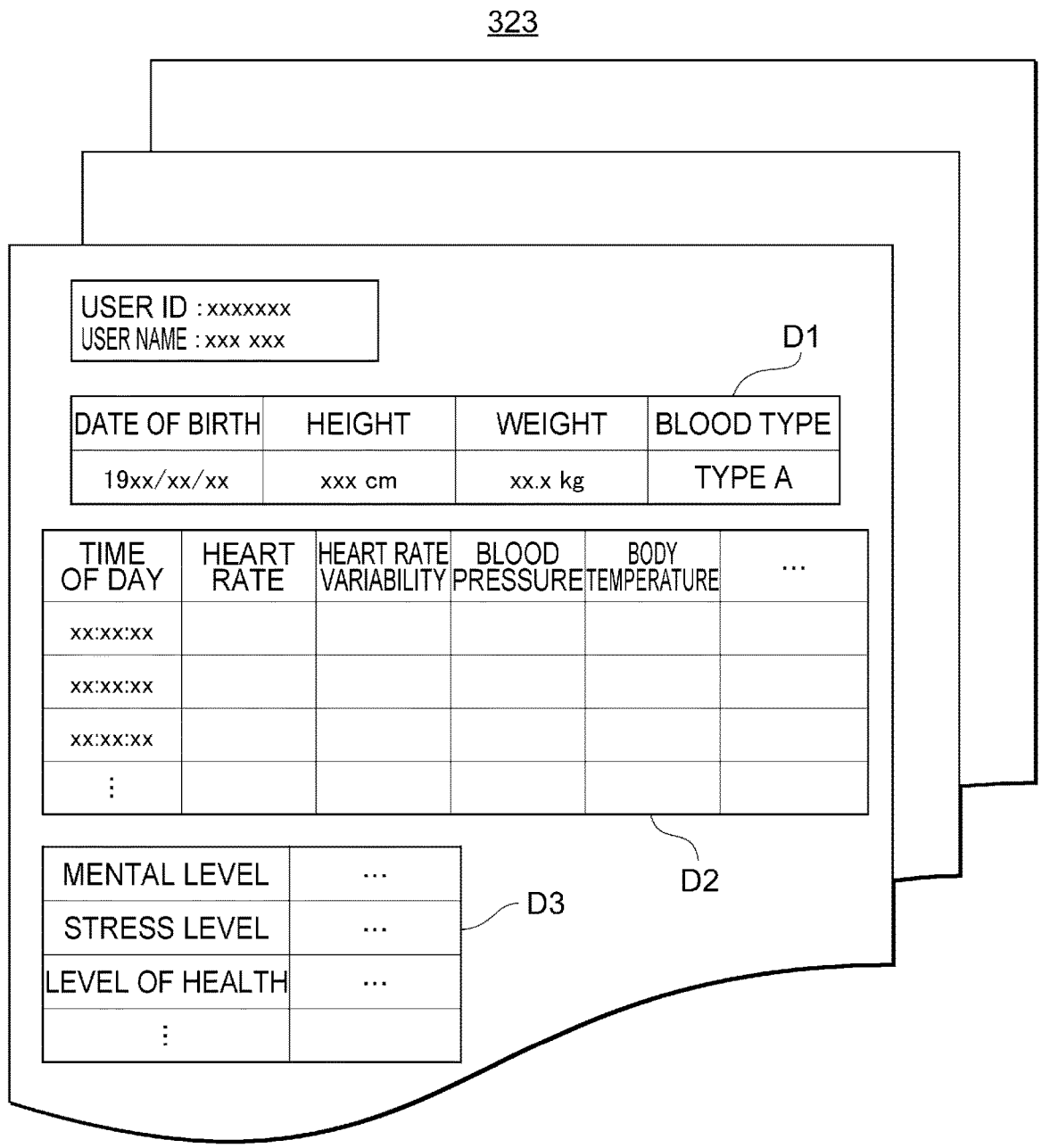
FIG. 5 is a schematic diagram illustrating information stored in a user information database stored in the storage unit shown in FIG. 3.

FIG. 5 is a schematic diagram illustrating information stored in the user information database 323. The user information database 323 stores, for each user ID, basic user information D1 including a birth date, a height, a weight, and a blood type of the user, vital data D2, and user state information D3 representing a state of the user estimated based on the vital data D2.

Among the information, the vital data D2 includes primary data directly acquired by the vital data collecting means 10 and secondary data acquired from the primary data. Primary data includes a heart rate, a pulse rate, blood pressure, body temperature, a movement of muscles of the face, the scalp, or the body, a movement of an eye or a pupil, and voice. In addition, secondary data includes a heart rate variability calculated from a heart rate, a facial expression or a bodily posture calculated from a movement of muscles of the face, the scalp, or the body, a movement of the diaphragm or a spinal extension calculated from a movement of muscles of the abdomen or the back, a variability of a movement of an eye calculated from the movement of the eye, and a change in a tone of voice (loudness, pitch, speed, and the like). The secondary data may be calculated at the user terminal 20 and transmitted to the information processing server 30 or may be calculated at the information processing server 30.

Since the vital data D2 is transmitted in real-time from the user terminal 20 and accumulated in the information processing server 30, the information processing server 30 may be configured to sequentially delete vital data D2 once a prescribed period (for example, a few years) elapses from reception of the vital data D2. Even in this case, user state information acquired from vital data to be deleted may be saved.

User state information D3 includes information representing a mental state such as emotions (joy, anger, sorrow, and pleasure) or a stress level, a state of health such as a health level or a location of discomfort, and a state of activity such as "asleep", "awake", "eating", or "exercising". These pieces of information may be represented by any of a numerical value converted from a level, textual (or symbolic) information, and a combination of a numerical value and textual (or symbolic) information.

Figure 6:
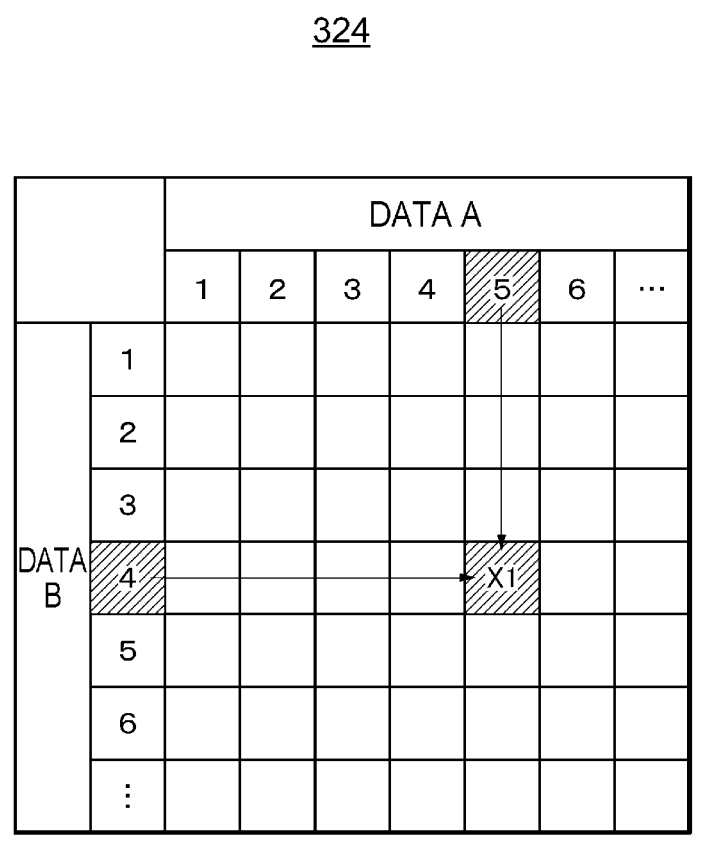

FIG. 6 is a schematic diagram illustrating information stored in the correlation information database 324. The correlation information database 324 stores information (correlation information) which associates vital data with a state (a mental state, a state of health, or a state of activity) of the user. Examples of correlation information include a table indicating a relationship between a plurality of mutually different types of vital data (in FIG. 6, data A and data B) and a state of the user at that time. FIG. 6 shows that, when a level of a certain piece of vital data (data A) is "5" and a level of another piece of vital data (data B) is "4", the state of the user is "X1".

A heart rate that is a piece of vital data fluctuates in accordance with a physical condition (for example, at normal body temperature as opposed to when fever is present), a mental state (for example, when calm as opposed to when nervous or excited), a state of activity (for example, during rest as opposed to during exercise), and the like. On the other hand, it is known that heartbeat intervals fluctuate to a certain degree in a normal state and that the fluctuation of heartbeat intervals becomes smaller when the mind or body is stressed or when autonomic function declines. In addition, in traditional Chinese medicine, it is common practice to determine a mental state (emotions or a stress level) and a state of health (a functional level of organs or the like) based on a heart rate and a heart rate variability.

In consideration thereof, measuring a heart rate and a rate of variability of heartbeat intervals (a heart rate variability) enables a mental state, a state of health, and a state of activity of the user to be estimated to a certain degree. Furthermore, using other vital data on the user (blood pressure, body temperature, a movement of an eye or a movement of facial muscles (a facial expression) of the user as captured by a camera, a change in a tone of voice, a movement of muscles of the body (a motion of the body), a movement of the diaphragm, a spinal extension, and the like) in combination with a heart rate and a heart rate variability enables the number of items that can be estimated with respect to the state of the user to be increased and, at the same time, enables estimation accuracy to be improved. For example, a state of activity such as asleep or awake can be estimated in addition to mental information and health information.

In this case, information used when estimating a state of the user need not be limited to vital data, and a state of the user estimated based on vital data (an estimation result) may be used. In other words, yet another state of the user may be estimated based on an estimation result based on vital data and on the vital data. For example, based on a stress level of the user estimated based on a heart rate and/or a heart rate variability and a movement of facial muscles, a mental state of the user can be estimated with greater detail.

The correlation information database 324 stores one or more pieces of correlation information used when estimating a state of the user in this manner. Moreover, correlation information need not necessarily take the form of a table, and a function having a plurality of types of vital data as variables or a function having an estimation result based on vital data and the vital data as variables may be stored as correlation information.

The correlation information stored in the correlation information database 324 may be created in advance based on external information or may be created based on the vital data accumulated in the information processing server 30. In addition, correlation information created in advance based on external information may be updated based on the vital data accumulated in the information processing server 30.

The processor 33 is constituted by an arithmetic logic operation unit (a CPU or the like) that processes arithmetic operations, logic operations, bit operations, and the like and various registers, and controls the respective units of the information processing server 30 in a concentrated manner by executing the various programs stored in the storage unit 32. Examples of the various registers include a program counter, a data register, an instruction register, and a general-purpose register. In addition, by executing the information processing program 321, the processor 33 realizes prescribed information processing functions in cooperation with the user terminal 20.

Functional units realized by the execution of the information processing program 321 by the processor 33 include an authentication managing unit 331, a user information managing unit 332, a user state estimating unit 333, an avatar data creating unit 334, and a correlation analyzing unit 335.

The authentication managing unit 331 performs authentication when the user terminal 20 accesses the information processing server 30. More specifically, when an access request is made by the user terminal 20, the authentication managing unit 331 requests the user terminal 20 to input a user ID and a passcode, and refers to the user management database 322 to authenticate whether or not an access by the user terminal 20 is to be permitted.

The user information managing unit 332 manages the user information database 323 based on information transmitted from the user terminal 20.

The user state estimating unit 333 estimates a state of the user based on vital data accumulated in the vital data D2 and on the correlation information database 324.

The avatar data creating unit 334 creates an avatar that is a character to be displayed on Internet space as an alter ego of the user and, at the same time, creates display data (hereinafter, referred to as avatar data) for reflecting vital data on the user and an estimation result (a state of the user) by the user state estimating unit 333 in an avatar and displaying the avatar. Types of the vital data and the state of the user to be reflected in the avatar and a display method of the avatar are not particularly limited. A display example of an avatar will be described later.

Since vital data is transmitted in real-time from the user terminal 20 and an estimated state of the user changes from moment to moment, the avatar is favorably displayed by animation. In addition, as avatar data, the avatar data creating unit 334 may create three-dimensional data including information representing an inside of the avatar and, in response to a request from the user terminal 20, construct display data on a state where the avatar is viewed from inside (for example, inside the gastrointestinal tract) or display data on a cross section whenever necessary.

The correlation analyzing unit 335 analyzes a correlation between pieces of vital data (input data) transmitted from the user terminal 20 and a correlation between vital data (input data) and an estimation result (output data) by the user state estimating unit 333 to construct a database of correlation information which associates vital data with states of the user.

Figure 7:
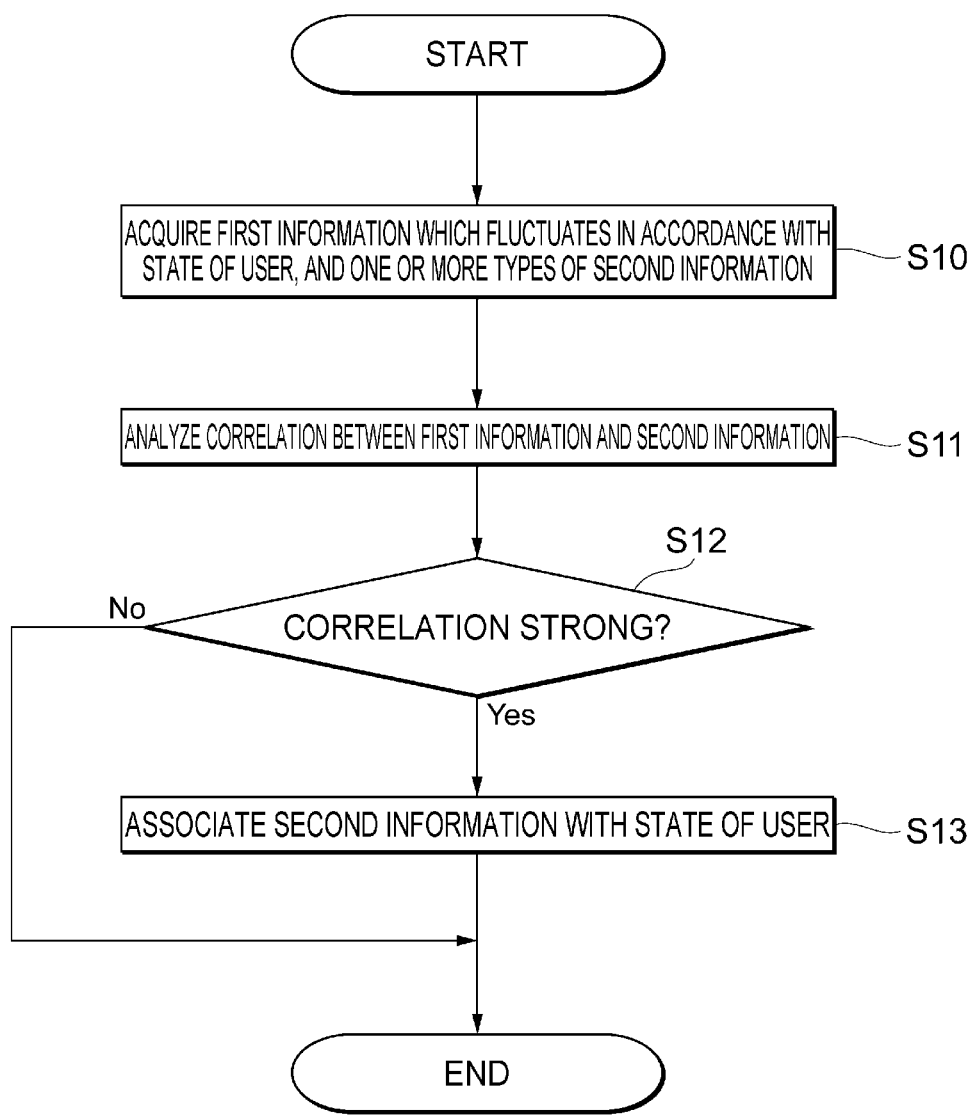
FIG. 7 is a flow chart showing a construction process of a correlation information database executed by a correlation analyzing unit shown in FIG. 3.

FIG. 7 is a flow chart showing a construction process of a correlation information database executed by the correlation analyzing unit 335.

First, in step S10, the correlation analyzing unit 335 acquires first information associated with a state of the user in advance, and one or more types of second information. At this point, as described earlier, since a heart rate variability is known to correlate with a stress level of the user, associating the heart rate variability with stress level in advance enables the heart rate variability to be used as the first information in step S10. In addition, as the second information, data other than a heart rate variability such as a movement of a specific region such as the eye, a change in tone of voice, a degree of swelling of the diaphragm, or spinal extension is acquired. The second information may be constituted by two or more mutually different types of information.

In subsequent step S11, the correlation analyzing unit 335 analyzes a correlation between the first information and the second information. In the example described above, a correlation between a heart rate variability and a movement of the eye, a correlation between a heart rate variability and a change in tone of voice, and a correlation between a heart rate variability and a movement of the diaphragm are analyzed.

In subsequent step S12, the correlation analyzing unit 335 determines whether or not the correlation between the first information and the second information is strong. For example, a strong correlation is determined when a coefficient of correlation between the two pieces of information is equal to or larger than a prescribed value, and a weak correlation is determined when the coefficient of correlation is smaller than the prescribed value.

When the correlation between the first information and the second information is weak (step S12: Yes), the correlation analyzing unit 335 ends the process.

On the other hand, when the correlation between the first information and the second information is strong (step S12: Yes), based on an analysis result of the correlation, the correlation analyzing unit 335 associates the second information with a state of the user having been associated with the first information in advance (step S13). More specifically, a table which associates the second information with a state of the user is created. Alternatively, a function having the second information as an input variable and a state of the user as an output value may be created. Accordingly, a state of the user can be directly estimated based on the second information. In the example described above, a stress level of the user can be estimated from data on a movement of the eye of the user without involving a heart rate variability. Alternatively, emotions of the user can be estimated from a change in the tone of voice. In addition, a degree of stress of the user can be estimated from a degree of swelling of the diaphragm or spinal extension. The correlation analyzing unit 335 accumulates correlation information between the second information and states of the user acquired in this manner in the correlation information database 324 (refer to FIG. 3). Subsequently, the correlation analyzing unit 335 ends the process.

As the first information, information other than a heart rate variability can be used as long as the information is associated with a state of the user. For example, once a movement of the eye and a stress level are associated with each other in step S13 described above, the movement of the eye can next be used as new first information in step S10. In this case, by using yet different vital data as the second information in step S11 and analyzing a correlation between the new first information and the second information, a stress level and the different vital data can be associated with each other via a movement of the eye.

In addition, an object of correlation analysis is not limited to a correlation between pieces of vital data, and a correlation between data arbitrarily input by the user and vital data or a correlation between data estimated from vital data and vital data may be analyzed. Specific examples include having the user input data such as a birth date, time and place of birth, a blood type, and a DNA profile of the user, a result of a divination (for example, Four Pillars Astrology), or the user's own assessment of vital data, and determining a correlation between such input data and vital data (a heart rate variability and the like).

By successively analyzing a correlation between pieces of vital data and a correlation between vital data and data other than vital data in this manner, a larger number of items can be estimated with respect to a state of the user (a mental state, a state of health, or a state of activity) and, at the same time, estimation accuracy can be improved. In addition, by reflecting the state of the user estimated in this manner in an avatar, an avatar more closely resembling a present state of the user can be displayed. Furthermore, by accumulating analysis results of such correlations, there is a possibility that a disease or the like which the user himself/herself is not aware of can be estimated.

In addition, by accumulating analysis results of a large number (for example, several hundred to several ten thousand) of users for a certain period of time (for example, one to a few years), a general trend related to states of users can be assessed. For example, a trend such as "users born in the month of B in area A are more likely to develop disease X" can be extracted.

Analysis results by the correlation analyzing unit 335 are accumulated in the correlation information database 324. Correlation information accumulated due to analysis by the correlation analyzing unit 335 may be used only to estimate a state of the user used for the analysis. Alternatively, correlation information that can be generalized may be used to estimate a state of other users.

(2) Operation of Embodiment

Figure 8:
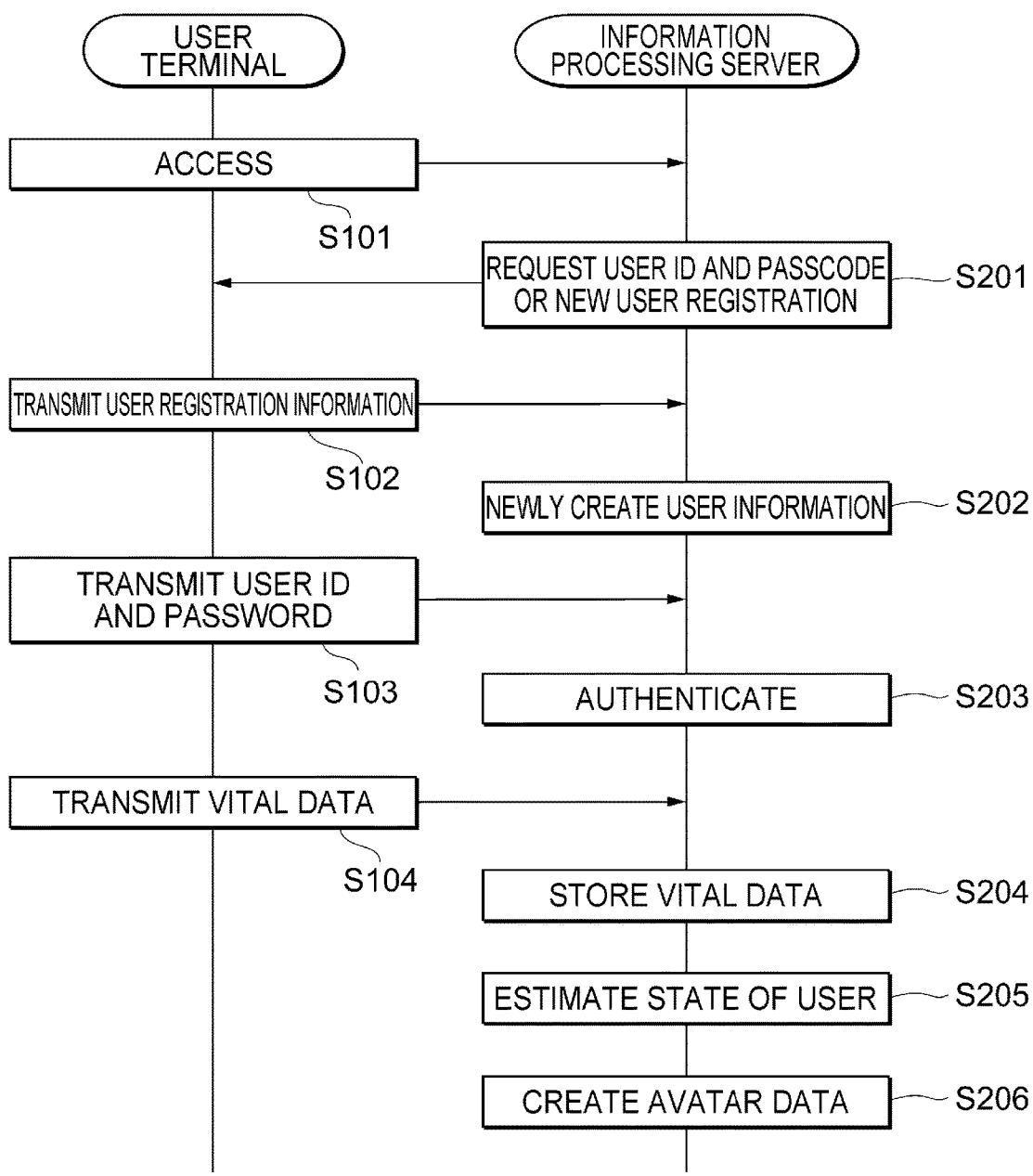
FIG. 8 is a sequence diagram of an information collection process executed in the information processing system shown in FIG. 1.

FIG. 8 is a sequence diagram of an information collection process executed in the information processing system 1 according to the embodiment of the present invention.

When the user terminal 20 makes a request to access the information processing server 30 (step S101), the information processing server 30 requests a user ID and a passcode or a new user registration from the user terminal 20 (step S201).

When the user terminal 20 transmits user registration information for new user registration (step S102), the information processing server 30 issues a user ID and a passcode and, at the same time, newly creates user information (step S202).

When a user ID and a passcode are transmitted from the user terminal 20 (step S103) and authentication succeeds at the information processing server 30 (step S203), the user terminal 20 changes to a log-in state in which vital data can be accumulated in the information processing server 30 from the user terminal 20.

When vital data collected by the vital data collecting means 10 (refer to FIG. 1) is transmitted from the user terminal 20 (step S104), the information processing server 30 receives the vital data and stores the vital data in the user information database 323 (step S204). Subsequently, the information processing server 30 estimates a state of the user (a mental state, a state of health, or a state of activity) based on accumulated vital data (step S205), and creates avatar data for displaying an avatar which reflects the state of the user (step S206).

Figure 9:
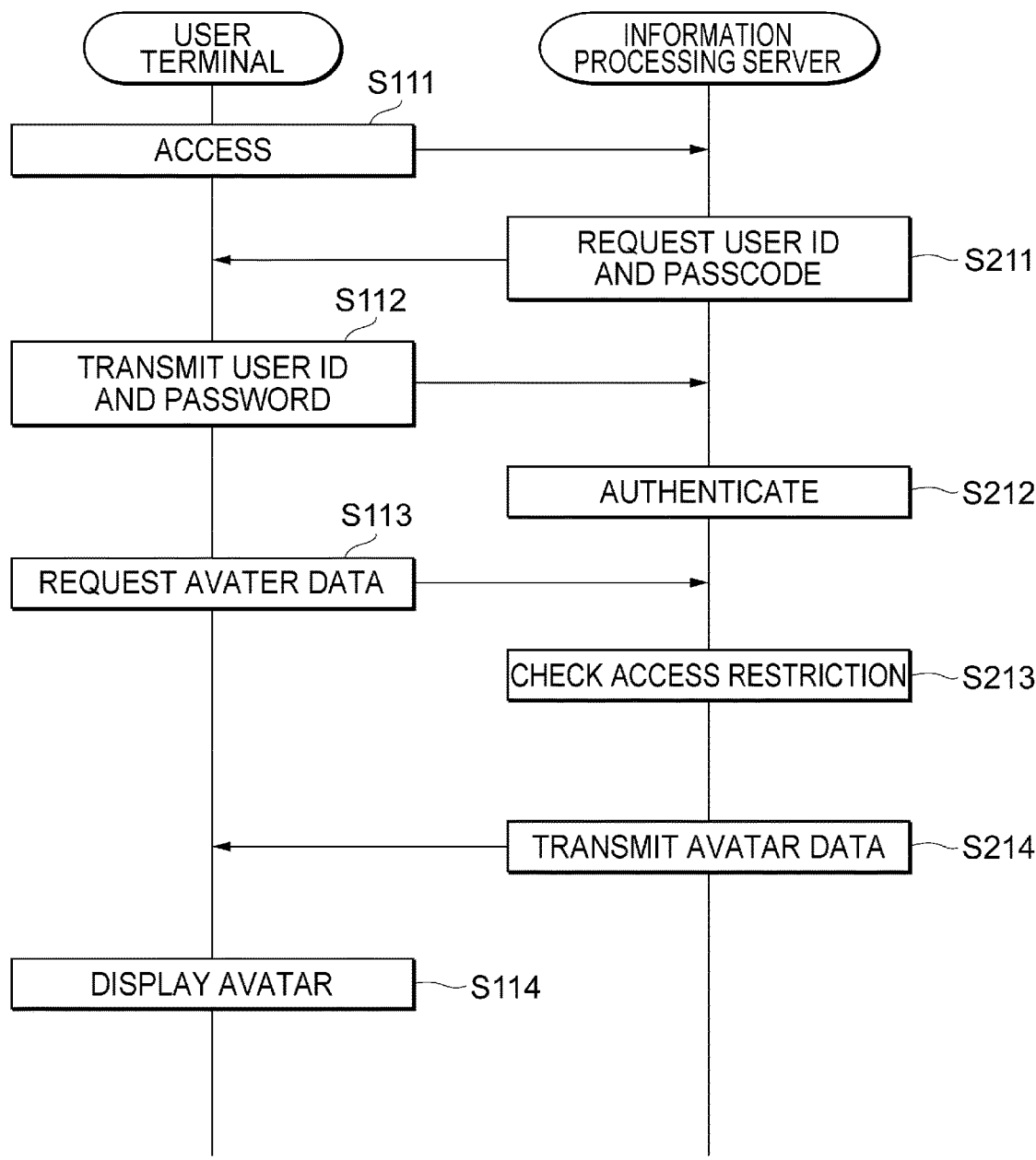
FIG. 9 is a sequence diagram of an avatar display process executed in the information processing system shown in FIG. 1.

FIG. 9 is a sequence diagram of an avatar display process executed in the information processing system 1 according to the embodiment of the present invention.

When the user terminal 20 makes a request to access the information processing server 30 (step S111), the information processing server 30 requests a user ID and a passcode from the user terminal 20 (step S211).

When a user ID and a passcode are transmitted from the user terminal 20 (step S112) and authentication succeeds at the information processing server 30 (step S212), the user terminal 20 changes to a log-in state. Moreover, when a log-in state of the user terminal 20 has been maintained, steps S112, S211, and S212 are omitted.

When the user terminal 20 makes a request for avatar data on a specific user to the information processing server 30 (step S113), the information processing server 30 refers to the user management database 322 and checks access restriction of the user for which avatar data is requested (step S213). In addition, the requested avatar data is transmitted to the user terminal 20 within a range of the access restriction (step S214). For example, when the access restriction is set to "only disclosed to user himself/herself", the information processing server 30 does not transmit the avatar data to anyone other than the user of the avatar data.

The user terminal 20 displays an avatar on a screen based on the received avatar data (step S114).

Figure 10:
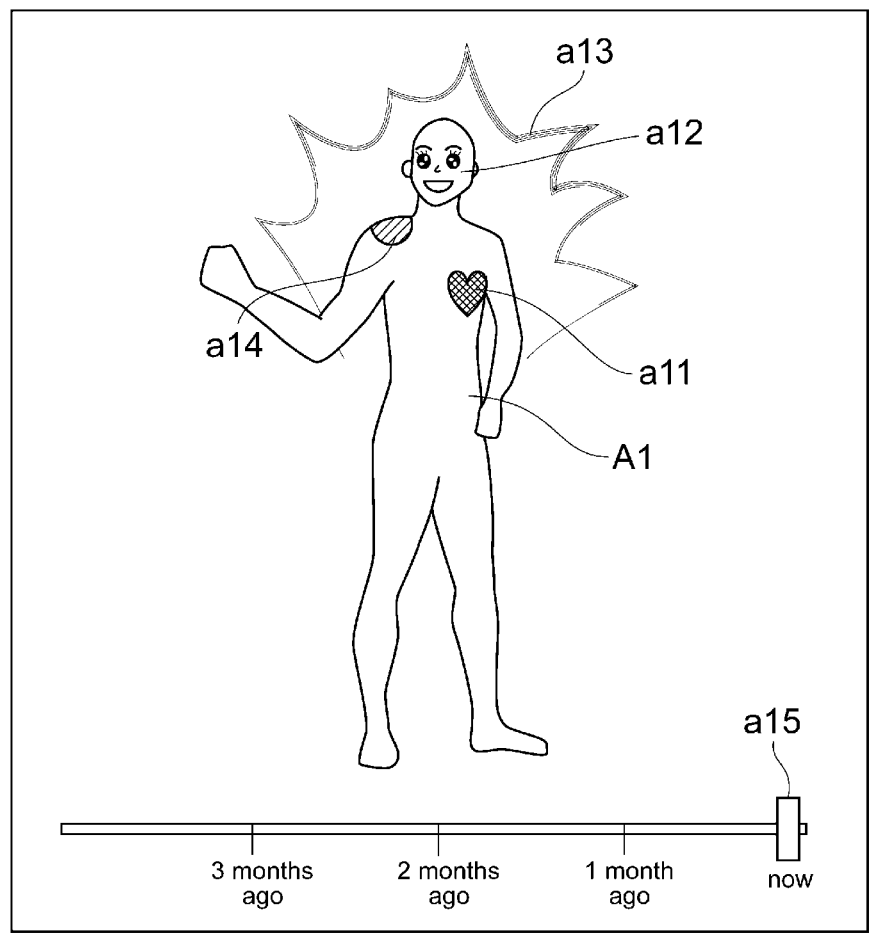
FIG. 10 is a schematic diagram showing a display example of an avatar.

FIG. 10 is a schematic diagram showing a display example of an avatar which is an avatar A1 emulating an entire human body. For example, a heart model a11 may be displayed superimposed on the avatar A1 and the heart model a11 may be pulsated in accordance with the heart rate of the user. In addition, an entire color of the avatar A1 may be changed in accordance with the body temperature of the user. Alternatively, an estimated mental state of the user (for example, emotions or a stress level) may be reflected in a facial expression or a color (a complexion) of a face a12 of the avatar A1. Furthermore, an estimated state of health of the user (for example, a level ranging from vitality to discomfort or a stress level) may be reflected in an aura (a halo) a13 of the avatar A1. As an example, a display range of the aura a13 is widened when the level of vitality is higher or a color of the aura a13 is changed in accordance with the stress level. In addition, a color of a portion of the avatar A1 corresponding to a location of discomfort in the body of the user may be changed in accordance with a degree of the discomfort. As an example, when stiffness in a shoulder of the user is severe, brightness of a shoulder portion a14 of the avatar A1 is reduced to display an occurrence of poor blood circulation. Furthermore, a shape of the avatar A1 may be changed in accordance with a state of activity of the user. As an example, a posture of the avatar A1 is changed in accordance with a movement of muscles of the user acquired from the surface myoelectric sensor 16 (refer to FIG. 1).

The avatar data creating unit 334 may change a form of the avatar A1 in accordance with a request transmitted from the user terminal 20. For example, a configuration may be adopted in which a slider a15 that is movable by an operation performed on the input unit 22 is displayed on the display unit 23 of the user terminal 20 and, when the slider a15 moves, information representing a position of the slider a15 is transmitted to the information processing server 30. The avatar data creating unit 334 creates avatar data reflecting previous vital data in accordance with the position of the slider a15, and transmits the created avatar data to the user terminal 20. Accordingly, the avatar A1 reflecting vital data on a period desired by the user is displayed on the user terminal 20. Enabling past avatars A1 to be also displayed in this manner makes it possible for the user to check a time-sequential change of a state of health and the like.

Alternatively, a configuration may be adopted in which, by performing a prescribed operation (for example, a tap operation) on the avatar A1 displayed on the display unit 23 of the user terminal 20, information indicating selection of a region in which the operation had been performed is transmitted to the information processing server 30. The avatar data creating unit 334 creates avatar data representing the inside (for example, an organ) of the selected region, and transmits the created avatar data to the user terminal 20. Accordingly, the avatar A1 with an internal region desired by the user being exposed is displayed on the user terminal 20. A display method of the internal region may be a method of showing a cross section of the avatar A1 or a method in which a small camera is apparently inserted into the avatar A1 and a video captured by the camera is shown.

Figure 11:
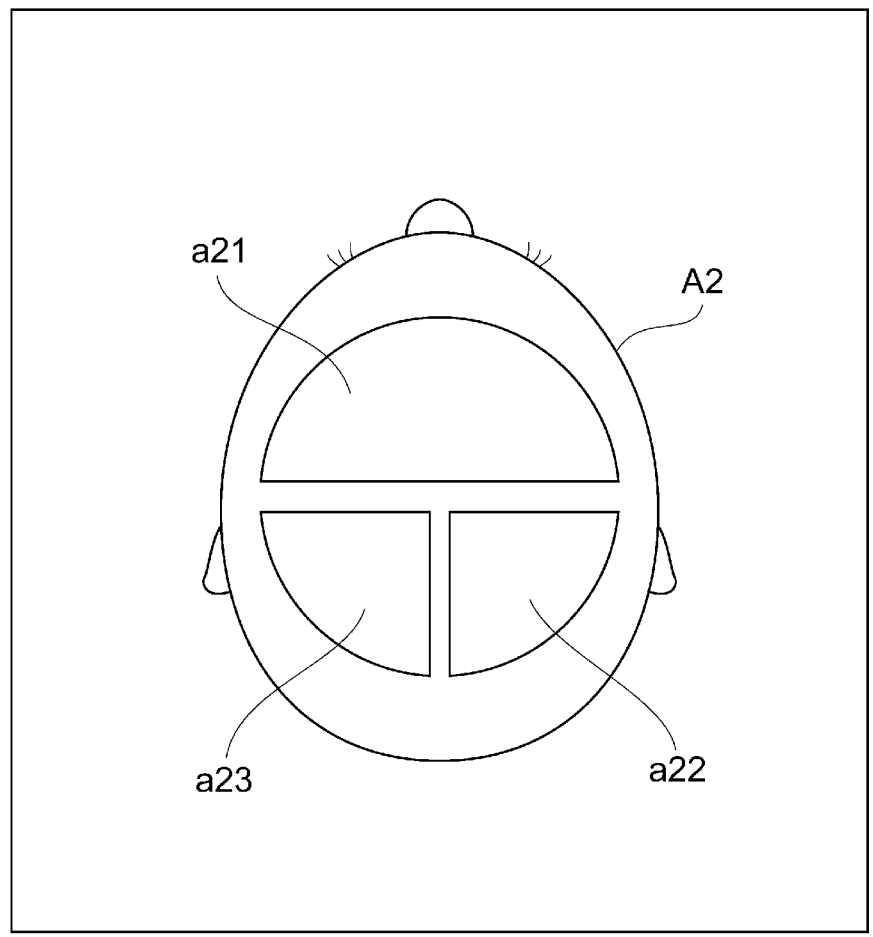
FIG. 11 is a schematic diagram showing another display example of an avatar.

FIG. 11 is a schematic diagram showing another display example of an avatar which is an avatar A2 emulating the head of the user. A region representing an emotion of the user (an emotion region a21), a region representing a state of activity of the right brain (a right-brain region a22), and a region representing a state of activity of the left brain (a left-brain region a23) are provided inside the avatar A2, and a size, a color, and the like of each region is changed in accordance with vital data or an estimated state of the user.

As described above, according to the present invention, since vital data at least including a heart rate of a user is acquired in real-time and avatar data is created based on a state of the user estimated in real-time based on the vital data, an avatar that more realistically reflects a state of the user can be constructed.

In addition, according to the present embodiment, since a correlation among a plurality of pieces of vital data and a correlation between an estimation result of a state of the user and vital data are analyzed and a state of the user is further estimated based on such correlations, the number of items that can be estimated with respect to the state of the user can be increased and, at the same time, estimation accuracy can be improved.

The information processing system 1 which displays an avatar based on vital data on a user in this manner can be utilized in various applications. As an example, by combining the information processing system 1 with an SNS (social networking system) such as "facebook (registered trademark)" or "LinkedIn (registered trademark)", an avatar can be used as a user profile.

Figures 12, 13:
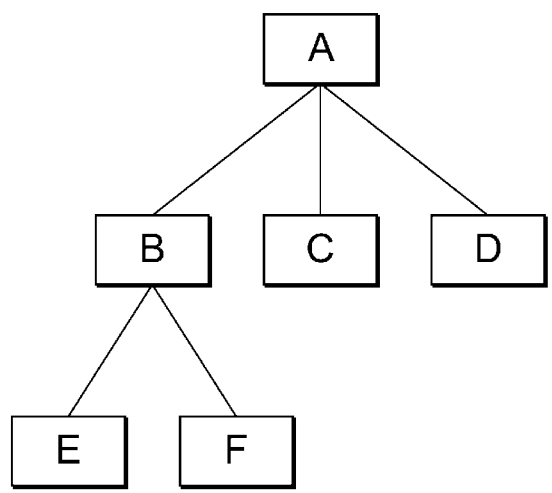
FIG. 12 is a diagram for explaining an example of utilization of the information processing system shown in FIG. 1 in an SNS.
FIG. 13 is a diagram for explaining an example of utilization of the information processing system shown in FIG. 1 in an SNS.

FIGS. 12 and 13 are diagrams for explaining an example of utilization of the information processing system 1 in an SNS. For example, as shown in FIG. 12, let us assume that a user A is connected as a "friend" to users B, C, and D on an SNS. In addition, let us assume that the user B is connected as a "friend" to users E and F in addition to the user A. A mental state, a state of health, or a state of activity of the users or an aura of each avatar is converted into a numeral value, and statistical values are calculated based on relationships of the users. For example, let us assume that aura values obtained by converting auras of avatars of the users A to F into numerical values are, respectively, 2, 3, 8, 5, 6, and 4. In this case, as shown in FIG. 13, a sum of the aura values of friends (the users B, C, and D) of the user A is 3+8+5=16, and an average value thereof is approximately 5.3. On the other hand, a sum of the aura values of friends (the users A, E, and F) of the user B is 2+6+4=12, and an average value thereof is approximately 4. Therefore, it is shown that the user A has friends with higher aura values than the user B.

In addition, by changing numerical values used for analysis, for example, an analysis such as "the user A has many friends with restless personalities or unhealthy friends" can be made. Alternatively, a comparison can be made between a work-based network and a private network of the user A. As numerical values used for analysis, vital data itself (a heart rate or the like) can be used in addition to numerical values converted from an aura, a mental state, a state of health, a state of activity, and the like. In addition, while an average value is used as a statistical value in the description given above, a median or a mode can be used instead.

Furthermore, in addition to a relationship connected by a network such as that exemplified in FIG. 12, the aura value, vital data, and the like described above may be acquired with respect to followers who follow posted articles or evaluators who evaluate the same, and the acquired aura values, vital data, and the like can be displayed in the form of points or rankings. Accordingly, for example, an analysis of a trend in followers or the like can be made such as "the followers of the user A have high stress levels" or "the followers of the user B have high health levels but low activity levels".

In addition, as another example, the information processing system 1 can be utilized in a recruitment site or a matchmaking site. In this case, an avatar may be presented to a company or a potential partner as a profile of a member (a job seeker or an individual seeking a partner).

Furthermore, as another example, the information processing system 1 can be utilized in a game site. For example, avatars can be pitted against one another in a battle game.

As yet another example, the information processing system 1 can be utilized in a health management application. In this case, even when a user is at a remote location, an indicator of a state of health of the user such as a pulse rate or body temperature can be acquired from an avatar displayed on the user terminal 20. In addition, an organ can be displayed in a state where the abdomen of the avatar is opened, or the gastrointestinal tract of the avatar can be displayed from the inside. Furthermore, a method of use such as a user correcting his or her own posture by looking at a posture of an entire body of the avatar can be adopted.

While a human being is assumed as a user of the information processing system 1 in the embodiment and modifications described above, an animal such as a pet or a farm animal may be adopted as a user. In other words, vital data collecting means is mounted to a dog, a cat, or the like, and an avatar of the animal is created based on collected vital data. In this case, a veterinarian can utilize the avatar by making a diagnosis while viewing the avatar.

It is to be understood that the embodiment described above is for illustrative purposes only and is not intended to limit the present invention thereto. In addition, various modifications can be made to the present invention without departing from the scope of the invention. For example, those skilled in the art will be able to replace resources (hardware resources or software resources) described in the embodiment by equivalents, in which case such replacements will also fall within the scope of the present invention.

REFERENCE SIGNS LIST

1 Information processing system
10 Vital data collecting means
11 Heart rate meter
12 Sphygmomanometer
13 Thermometer
14 Web camera
15 Surface myoelectric sensor
20 User terminal
21 Communication interface
22 Input unit
23 Display unit
24 Imaging unit
25 Signal input/output unit
26 Storage unit
27 Processor
30 Information processing server
31 Communication interface
32 Storage unit
33 Processor
261 Application program
271 Application executing unit
321 Information processing program
322 User management database
323 User information database
324 Correlation information database
331 Authentication managing unit
332 User information managing unit
333 User state estimating unit
334 Avatar data creating unit
335 Correlation analyzing unit

What is claimed is:

1. An information processing system, comprising:
vital data acquiring means for acquiring vital data on a user;
a terminal apparatus that transmits, via a communication network, the vital data acquired by the vital data acquiring means; and
an information processing server that processes the vital data transmitted from the terminal apparatus, wherein the information processing server includes:
a storage unit that stores the vital data;
a user state estimating unit that analyzes a correlation between first vital data including a heart rate and a heart rate variability, which represents a variability of heartbeat intervals, wherein the first vital data is associated with a state of the user and second vital data of a different type from the first vital data, wherein the second vital data comprises at least one vital data selected from body temperature, movement of a muscle, movement of an eye, and voice, and that estimates a state of the user based on an analysis result thereof, wherein the user state estimating unit analyzes the correlation by calculating a coefficient of correlation between the first vital data and the second vital data and determining whether the coefficient of correlation is equal to or larger than a prescribed value, and when the coefficient of correlation is equal to or larger than the prescribed value the user state estimating unit associates the second vital data with the state of the user associated with the first vital data;

an avatar data creating unit that creates display data for displaying an avatar reflecting the state of the user directly estimated based on the second vital data; and a communication interface that, when a transmission request for the display data is received via the communication network, transmits the display data to a source of the transmission request, the information processing system being capable of causing an avatar reflecting the state of the user to be displayed at the request source, wherein the display data is three-dimensional data including information relating to an inside of the avatar, and display data for displaying the inside of the avatar is created and transmitted to the request source in response to a transmission request for the display data from the request source.

2. An information processing server, comprising:

a storage unit that stores first vital data received from a terminal apparatus via a communication network and including a heart rate and a heart rate variability, which represents a variability of heartbeat intervals, of a user;

a user state estimating unit that analyzes a correlation between the first vital data including the heart rate and the heart rate variability, wherein the first vital data is associated with a state of the user and second vital data of a different type from the first vital data, wherein the second vital data comprises at least one vital data selected from body temperature, movement of a muscle, movement of an eye, and voice, and that estimates a state of the user, wherein the user state estimating unit calculates a coefficient of correlation between the first vital data and the second vital data, and determines whether the coefficient of correlation is equal to or larger than a prescribed value, and when the coefficient of correlation is equal to or larger than the prescribed value the user state estimating unit associates the second vital data with the state of the user associated with the first vital data;

an avatar data creating unit that creates display data for displaying an avatar reflecting the state of the user directly estimated based on the second vital data; and a communication interface that, when a transmission request for the display data is received via the communication network, transmits the display data to a source of the transmission request, the information processing system being capable of causing an avatar reflecting the state of the user to be displayed at the request source, wherein the display data is three-dimensional data including information relating to an inside of the avatar, and display data for displaying the inside of the avatar is created and transmitted to the request source in response to a transmission request for the display data from the request source.

3. The information processing server according to claim 2, wherein the avatar data creating unit creates display data on the avatar reflecting previous vital data in accordance with information input at the request source, and by having the communication interface transmit the display data on the avatar reflecting the previous vital data to the request source, a time-sequential change of the state of the user can be checked at the request source.

4. The information processing server according to claim 2, wherein the user state estimating unit estimates a mental state of the user, and the avatar data creating unit creates display data on the avatar reflecting the mental state of the user.

5. The information processing server according to claim 2, wherein the user state estimating unit estimates a state of health of the user, and the avatar data creating unit creates display data on the avatar reflecting the state of health of the user.

6. The information processing server according to claim 2, wherein the user state estimating unit estimates a state of activity of the user, and the avatar data creating unit creates display data on the avatar reflecting the state of activity of the user.

7. An information processing method in an information processing server including a processor and a storage unit, the information processing method comprising, by operating the processor:

receiving first vital data including a heart rate and a heart rate variability, which represents a variability of heartbeat intervals, of a user from a terminal apparatus via a communication network;

storing the received heart rate and heart rate variability in the storage unit;

analyzing a correlation between the first vital data including the heart rate and the heart rate variability, wherein the first vital data is associated with a state of the user and second vital data of a different type from the first vital data, wherein the second vital data comprises at least one vital data selected from body temperature, movement of a muscle, movement of an eye, and voice, and estimating a state of the user, based on the analysis result thereof, wherein analyzing the correlation includes calculating a coefficient of correlation between the first vital data and the second vital data, determining whether the coefficient of correlation is equal to or larger than a prescribed value, and, when the coefficient of correlation is equal to or larger than the prescribed value, associating the second vital data with the state of the user associated with the first vital data;

creating display data for displaying an avatar reflecting the state of the user directly estimated based on the second vital data; and transmitting, when a transmission request for the display data is received via the communication network, the display data to a source of the transmission request, the information processing method enabling an avatar reflecting the state of the user to be displayed at the request source, wherein the display data is three-dimensional data including information relating to an inside of the avatar, and display data for displaying the inside of the avatar is created and transmitted to the request source in response to a transmission request for the display data from the request source.

8. A non-transitory computer readable medium comprising a program causing a computer to:

receive first vital data including a heart rate and a heart rate variability, which represents a variability of heartbeat intervals, of a user from a terminal apparatus via a communication network;

store the received heart rate and heart rate variability in the storage unit;

calculate a coefficient of correlation between the first vital data including the heart rate and the heart rate variability, wherein the first vital data is associated with a state of the user, and second vital data of a different type from the first vital data, wherein the second vital data comprises at least one vital data selected from body temperature, movement of a muscle, movement of an eye, and voice whether the coefficient of correlation is equal to or larger than a prescribed value, and when the coefficient of correlation is equal to or larger than the prescribed value, associate the second vital data with the state of the user associated with the first vital data;

create display data for displaying an avatar reflecting the state of the user directly estimated based on the second vital data; and transmit, when a transmission request for the display data is received via the communication network, the display data to a source of the transmission request, the program enabling the computer to cause an avatar reflecting the state of the user to be displayed at the request source, wherein the display data is three-dimensional data including information relating to an inside of the avatar, and display data for displaying the inside of the avatar is created and transmitted to the request source in response to a transmission request for the display data from the request source.

9. The information processing server according to claim 2, wherein the display data is for displaying a cross section of the avatar.

10. The information processing server according to claim 2, wherein the display data is for displaying an internal region of the avatar so as to have the appearance of a camera inserted into the avatar.

11. The information processing server according to claim 2, wherein the display data is for displaying an internal region of the avatar so as to have the appearance of a video camera inserted into the avatar.

* * * * *